(12) United States Patent
Helebert et al.

(10) Patent No.: US 12,239,341 B2
(45) Date of Patent: Mar. 4, 2025

(54) TISSUE-REMOVING CATHETER WITH A COUPLED INNER LINER

(71) Applicant: MEDTRONIC VASCULAR, INC., Santa Rosa, CA (US)

(72) Inventors: Rebecca Marie Helebert, Galway (IE); Thomas P. Hayden, Galway (IE); Aram Jamous, Galway (IE); Conor McMullen, Galway (IE); Tomas K. Kelly, Galway (IE); Michael James Donegan, Galway (IE); Eoin J. Walsh, Galway (IE); Aran Murray, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 408 days.

(21) Appl. No.: 17/654,230

(22) Filed: Mar. 9, 2022

(65) Prior Publication Data

US 2022/0313307 A1 Oct. 6, 2022

Related U.S. Application Data

(60) Provisional application No. 63/167,834, filed on Mar. 30, 2021.

(51) Int. Cl.
*A61B 17/3207* (2006.01)
*A61B 17/00* (2006.01)

(52) U.S. Cl.
CPC ........... *A61B 17/320758* (2013.01); *A61B 2017/00336* (2013.01); *A61B 2017/00398* (2013.01);

(Continued)

(58) Field of Classification Search
CPC .. A61B 17/320758; A61B 2017/00199; A61B 2017/0042; A61B 2017/00526;
(Continued)

(56) References Cited

U.S. PATENT DOCUMENTS

2005/0203527 A1 9/2005 Carrison et al.
2007/0250053 A1 10/2007 Fernald et al.
(Continued)

FOREIGN PATENT DOCUMENTS

CN 210044084 U 2/2020

OTHER PUBLICATIONS

Extended European Search Report for Application No. 22165290.2, Aug. 16, 2022, 7 pages, München, Germany.
(Continued)

*Primary Examiner* — Shaun L David
*Assistant Examiner* — Rachael L Geiger
(74) *Attorney, Agent, or Firm* — Stinson LLP

(57) ABSTRACT

A tissue-removing catheter for removing tissue in a body lumen includes an elongate body having an axis. A handle is mounted to a proximal end portion of the elongate body. A tissue-removing element is mounted on a distal end portion of the elongate body. An inner liner is received within the elongate body and defines a guidewire lumen. An advancer is mounted on the handle and is movable relative to the housing. The inner liner is coupled to the advancer at a proximal end portion of the inner liner such that movement of the advancer causes a corresponding movement of the inner liner to exert a push force on the tissue-removing element to advance the tissue-removing element and a pull force on the tissue-removing element to retract the tissue-removing element for moving the tissue-removing element relative to the handle.

14 Claims, 18 Drawing Sheets

(52) U.S. Cl.
CPC .............. *A61B 2017/00477* (2013.01); *A61B 2017/00876* (2013.01)

(58) Field of Classification Search
CPC ......... A61B 2017/00964; A61B 2017/320004; A61B 2017/00336; A61B 2017/00398; A61B 2017/00477; A61B 2017/00876; A61B 2017/22049
See application file for complete search history.

(56) References Cited

U.S. PATENT DOCUMENTS

| | | |
|---|---|---|
| 2009/0204021 A1 | 8/2009 | Shabaz et al. |
| 2009/0222023 A1* | 9/2009 | Boone, III ........... A61B 17/545 606/131 |
| 2012/0109171 A1 | 5/2012 | Zeroni et al. |
| 2012/0239066 A1 | 9/2012 | Levine |
| 2016/0331645 A1 | 11/2016 | Bagwell et al. |
| 2017/0273698 A1 | 9/2017 | Mcguckin, Jr. et al. |
| 2017/0273711 A1 | 9/2017 | Simpson et al. |
| 2018/0317952 A1 | 11/2018 | Jamous et al. |
| 2019/0046228 A1 | 2/2019 | Jamous et al. |
| 2019/0321045 A1 | 10/2019 | Sgroi, Jr. et al. |
| 2020/0155194 A1* | 5/2020 | Schneider ...... A61B 17/320725 |
| 2020/0360047 A1* | 11/2020 | Kelly ............. A61B 17/320758 |
| 2021/0069468 A1 | 3/2021 | Keating et al. |

OTHER PUBLICATIONS

Notice of First Office Action for Chinese Application No. 202110924050.9, Mar. 16, 2024, 13 pages with English translation.

Second Office Action, and translation thereof, from CN Application No. 202110924050.0, dated Aug. 9, 2024 16 pages.

* cited by examiner

TISSUE-REMOVING CATHETER WITH A COUPLED INNER LINER

CROSS-REFERENCE TO RELATED APPLICATION

This application claims the benefit of U.S. Provisional Patent Application Ser. No. 63/167,834, filed on Mar. 30, 2021, the entire contents of which are hereby incorporated by reference.

FIELD

The present disclosure generally relates to a tissue-removing catheter, and more particular, to a coupled inner liner of a tissue-removing catheter.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

SUMMARY

In one aspect, a tissue-removing catheter for removing tissue in a body lumen generally comprises an elongate body having an axis, and proximal and distal end portions spaced apart from one another along the axis. The elongate body is sized and shaped to be received in the body lumen. A handle is mounted to the proximal end portion of the elongate body. The handle comprises a housing enclosing components operable to cause rotation of the elongate body. A tissue-removing element is mounted on the distal end portion of the elongate body. The tissue-removing element is configured to remove the tissue as the tissue-removing element is rotated by the elongate body within the body lumen. An inner liner is received within the elongate body and defines a guidewire lumen. An advancer is mounted on the handle and is movable relative to the housing. The inner liner is coupled to the advancer at a proximal end portion of the inner liner such that movement of the advancer causes a corresponding movement of the inner liner to exert a push force on the tissue-removing element to advance the tissue-removing element and a pull force on the tissue-removing element to retract the tissue-removing element for moving the tissue-removing element relative to the handle.

BRIEF DESCRIPTION OF THE DRAWINGS

Corresponding reference characters indicate corresponding parts throughout the drawings.

DETAILED DESCRIPTION

Figure 1:
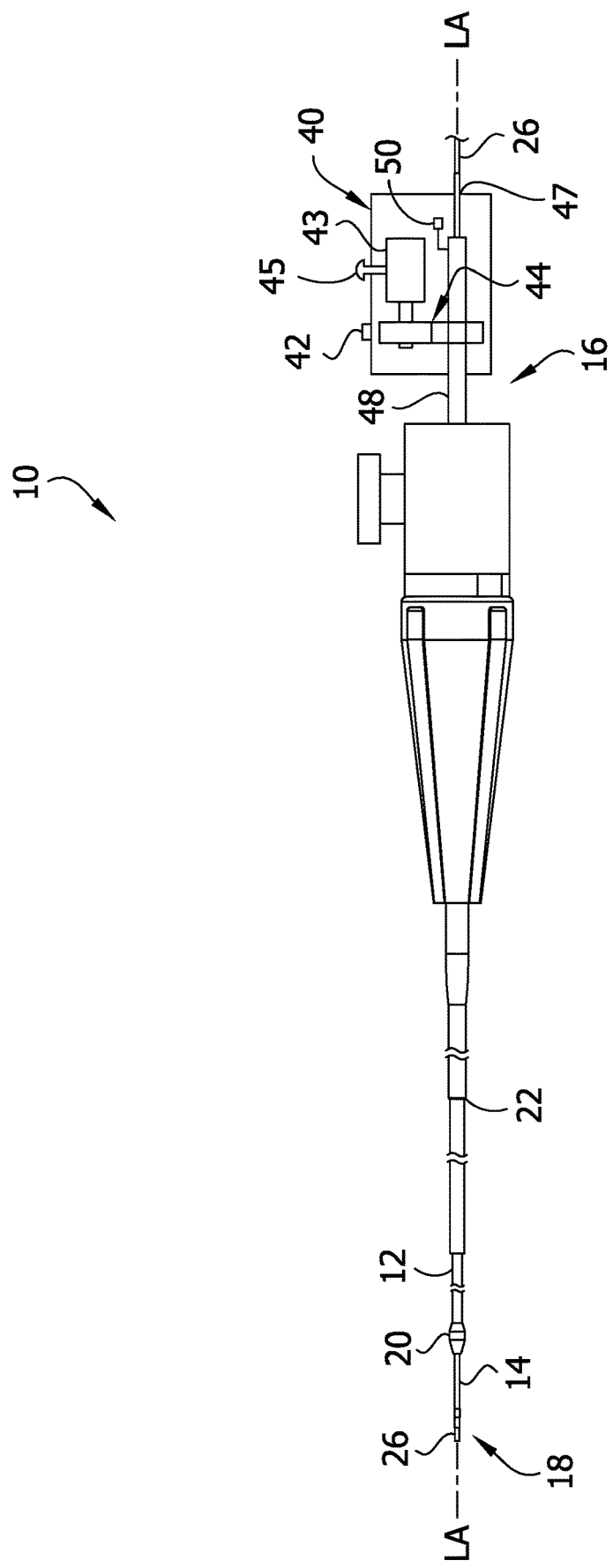
FIG. 1 is a schematic illustration of a catheter of the present disclosure.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
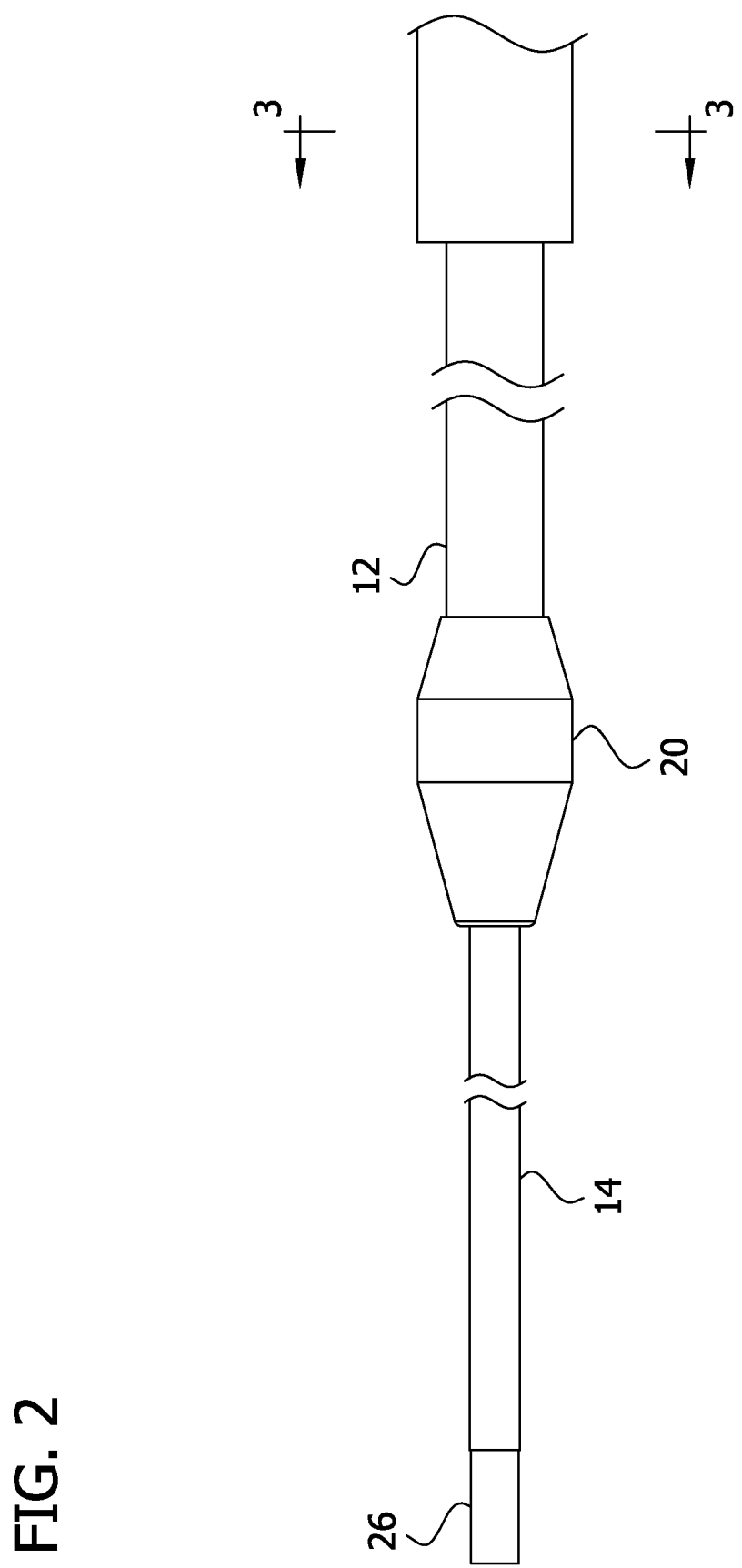
FIG. 2 is an enlarged elevation of a distal end portion of the catheter.
Figure 3:
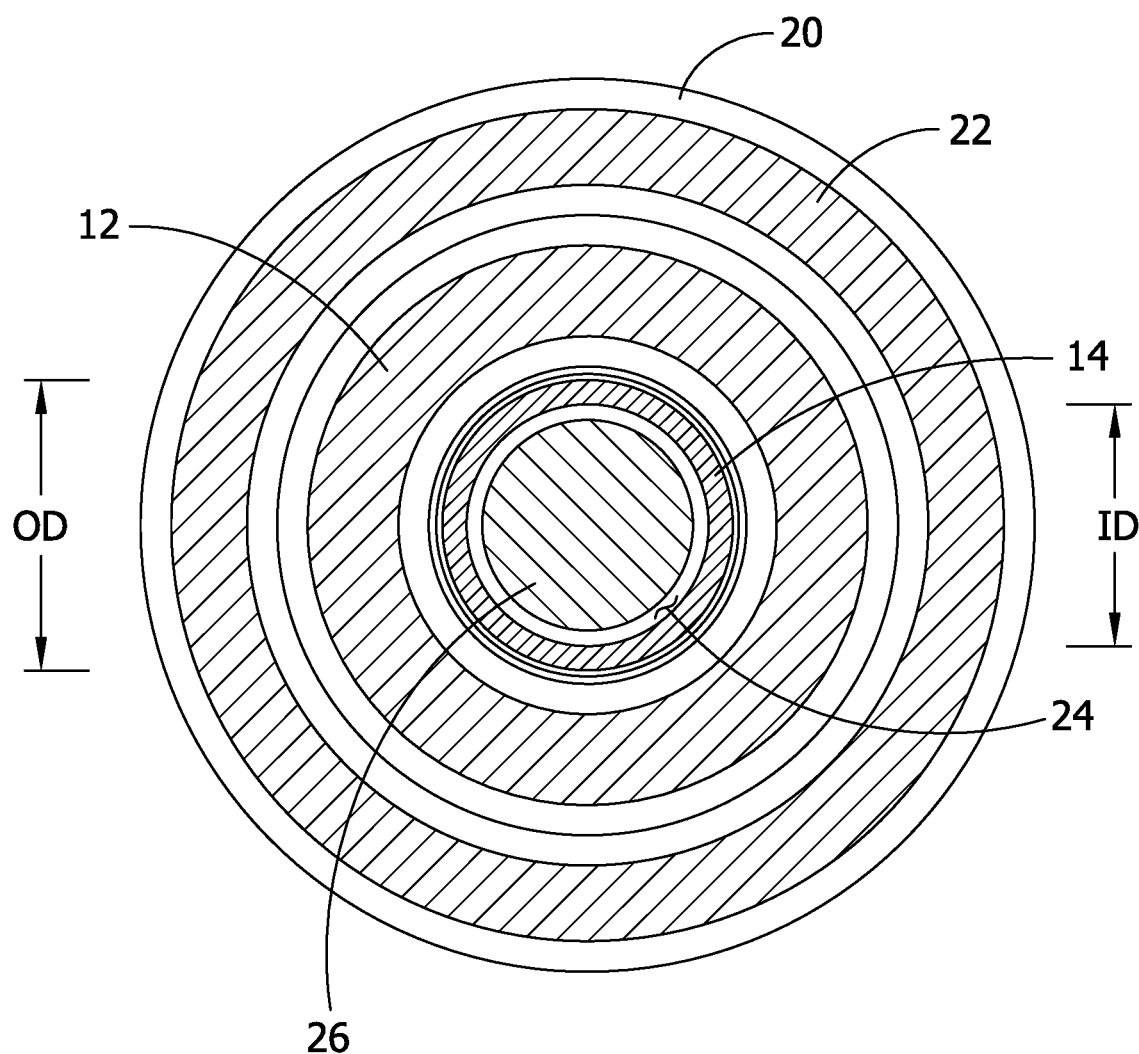
FIG. 3 is a cross section taken through line 3-3 in FIG. 2.

Referring to FIGS. 1-3, the catheter 10 comprises an elongate drive coil 12 (broadly, an elongate body) disposed around an elongate inner liner 14. The drive coil 12 and inner liner 14 extend along a longitudinal axis LA of the catheter from a proximal end portion 16 to a distal end portion 18 of the catheter. A tissue-removing element 20 is disposed on a distal end of the drive coil 12 and is configured for rotation to remove tissue from a body lumen as will be explained in greater detail below. An isolation sheath 22 is disposed around the drive coil 12. The drive coil 12 and the inner liner 14 are both configured to translate relative to the isolation sheath 22. The catheter 10 is sized and shaped for insertion into a body lumen of a subject. The isolation sheath 22 isolates the body lumen from at least a portion of the drive coil 12 and inner liner 14. The inner liner 14 defines a guidewire lumen 24 (FIG. 3) for slidably receiving a guidewire 26 therein so that the catheter 10 can be advanced through the body lumen by traveling along the guidewire. The guidewire can be a standard 0.014-inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends along an entire working length of the catheter 10. In one embodiment, the overall working length of the catheter 10 may be between about 135 cm (53 inches) and about 142 cm (56 inches). In use, the guidewire 26 may extend about 40 mm (1.6 inches) past a distal end of the inner liner 14.

Referring to FIGS. 1 and 4-7, the catheter 10 further comprises a handle 40 secured at a proximal end of the isolation sheath 22. The handle 40 comprises a housing 41 that supports the components of the handle. The housing 41 has a generally elongate egg shape and includes a plurality of housing sections secured together to enclose the internal components of the handle 40. In the illustrated embodiment, the housing 41 includes a bottom housing section 41A, a middle housing section 41B secured to the top of the bottom housing section, and a top housing section 41C secured to the top of the middle housing section. In one embodiment, the bottom housing section 41A is removable from the middle housing section 41B to provide access to the components of the handle 40 in the interior of the housing 41 by a user. It will be understood that the housing 41 can have other shapes and configurations without departing from the scope of the disclosure.

The housing 41 supports an actuator 42 (e.g., a lever, a button, a dial, a switch, or other device) configured for selectively actuating a motor 43 disposed in the handle to drive rotation of the drive coil 12, and the tissue-removing element 20 mounted at the distal end of the drive coil. The motor 43 is configured to rotate the drive coil 12 and tissue-removing element 20 at speeds of greater than about 80,000 RPM. In one embodiment, the motor 43 rotates the drive coil 12 and tissue-removing element 20 between about 10,000 and about 110,000 RPM. The motor 43 is coupled to the drive coil 12 by a gear assembly 44 and drive assembly 48 supported within the housing 41. The gear assembly 44 comprises a gearbox housing 55 that mounts and at least partially encloses a pair of gears for transferring the rotation of a shaft of the motor 43 to the drive coil 12.

Figure 6:
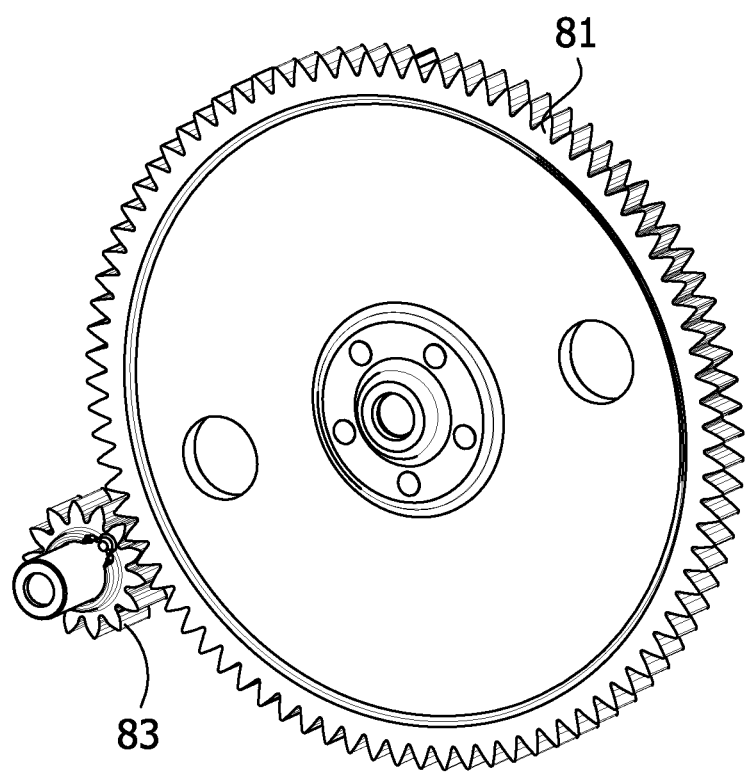
FIG. 6 is a perspective of gears of a gear assembly in the handle.

The motor 43 is coupled to the drive coil 12 by a gear assembly 44 and drive assembly 48 supported within the housing 41. The gear assembly 44 comprises a gearbox housing 55 that mounts and at least partially encloses a pair of gears for transferring the rotation of a shaft of the motor 43 to the drive coil 12. The gearbox housing 55 includes a rear housing section 61 and a front housing section 63 formed integrally with the rear housing section such that the gearbox housing comprises a single housing structure (FIG. 7). The rear housing section 61 incudes a tube sleeve portion 69 on the proximal side of the rear housing section that receives a distal end portion of a guide tube 223. The rear housing section 61 also attaches to a carriage or advancer frame 73 for moving the motor 43 and gear assembly 44 within the housing 41. Further, attaching the gearbox housing 55 to the distal end of the advancer frame 73 secures the motor 43 in the advancer frame so that the motor moves along with the advancer frame. The front housing section 63 has a distal sleeve portion that receives a portion of drive assembly 48. A driver gear 81 is attached to the motor 43 such that the driver gear rotates with the motor shaft when the motor 43 is activated (FIG. 6). A driven gear 83 is in mesh with the driver gear 81 so that rotation of the driver gear causes the driven gear to rotate in the opposite direction. The drive assembly 48 attaches the driven gear 83 to the drive coil 12 so that the rotation of the driven gear causes the drive coil to rotate. A controller 50 may be provided in the handle 40. The controller 50 may be programmed to control operation of the catheter.

It is understood that other suitable actuators, including but not limited to touchscreen actuators, wireless control actuators, automated actuators directed by a controller, etc., may be suitable to selectively actuate the motor in other embodiments. In some embodiments, a power supply may come from a battery (not shown) contained within the handle 40. The battery can provide the current source for the guidewire detection circuit. In other embodiments, the power supply may come from an external source.

Figure 4:
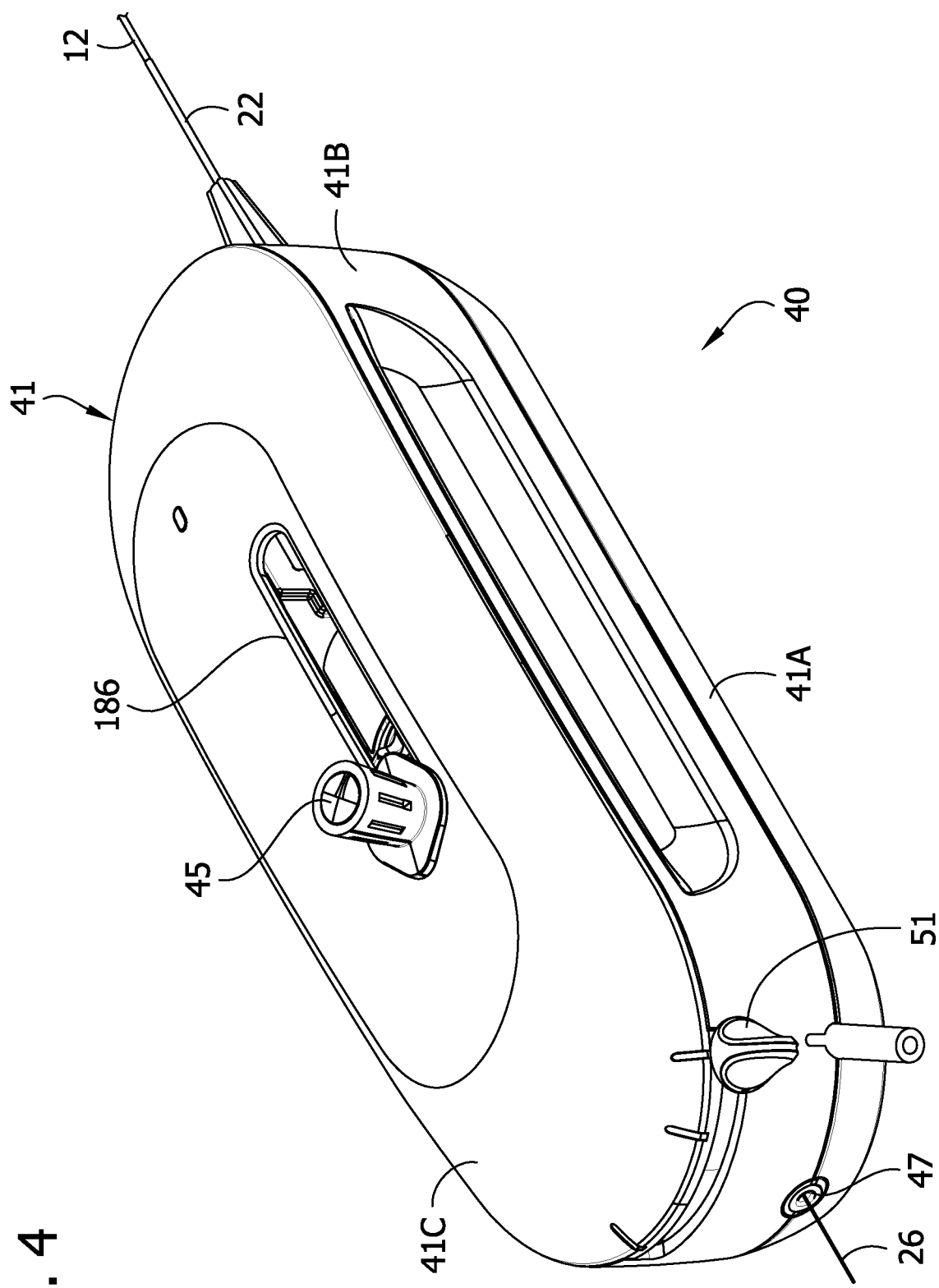
FIG. 4 is a top perspective of a handle of the catheter.
Figure 5:
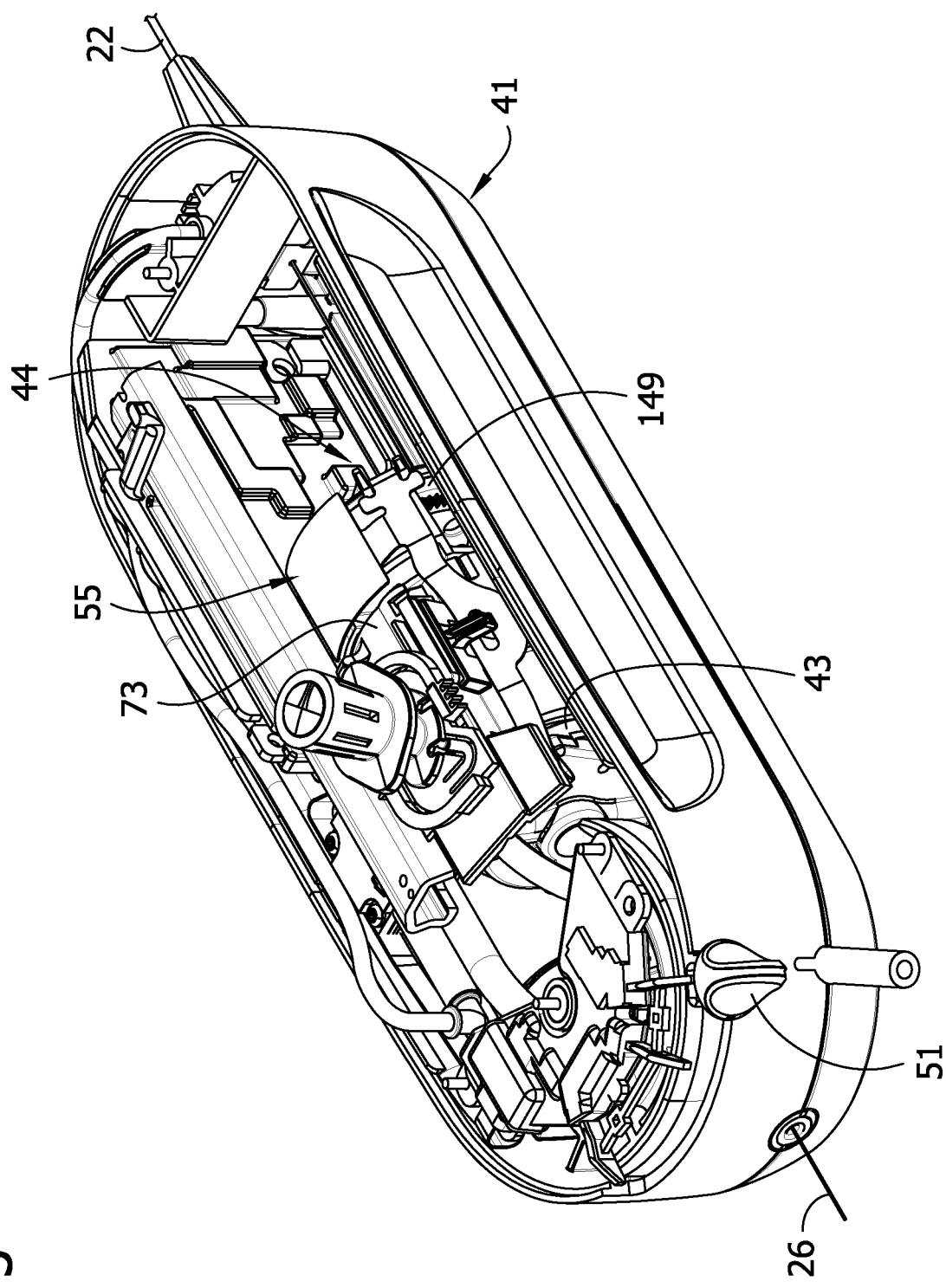
FIG. 5 is a top perspective of the handle with a top housing section removed.

Referring to FIGS. 1, 4, and 5, a slide or advancer 45 is positioned on the handle 40 and is operatively coupled to the inner liner 14 for movement of the inner liner relative to the handle to advance and retract the inner liner, drive coil 12, and tissue-removing element 20. The housing 41 of the handle 40 may define a slot 186 which limits the movement of the slide 45 relative to the handle. Thus, the length of the slot 186 determines the amount of relative movement between the inner liner 14 and the handle 40. In one embodiment, the slot has a length of about 70 mm (2.8 inches). The slide 45 is operatively attached to the advancer frame 73 so that movement of the slide causes movement of the advancer frame. The advancer frame 73 comprises an arch shaped body configured to slidingly receive the cylindrically shaped motor 43. Bearings 149 (FIG. 5) are mounted on the frame 73. The bearings 149 engage the housing 41 so that the bearings can slide along the housing to facilitate movement of the frame 73 in the housing.

Figure 7A:
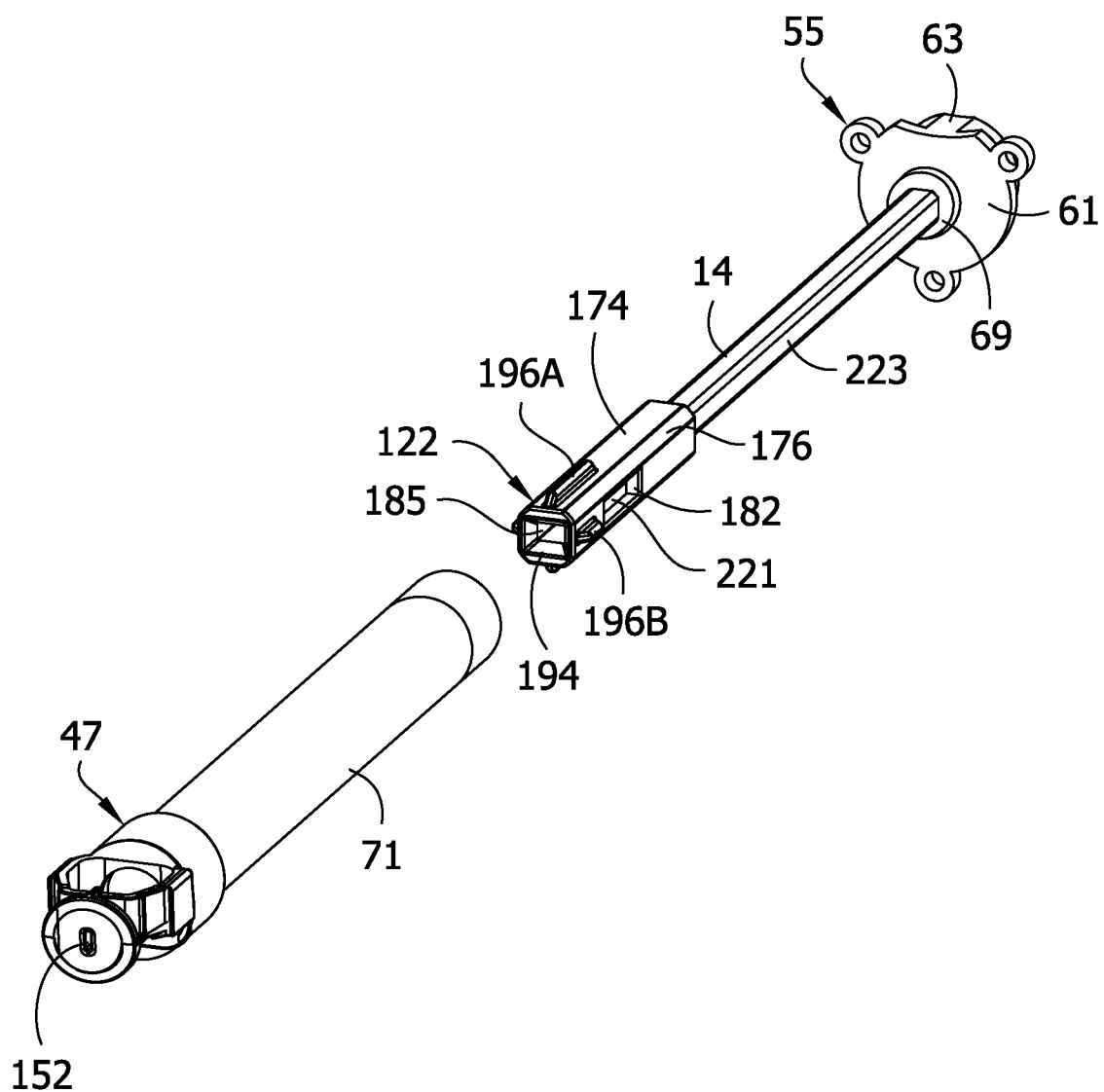
FIG. 7A is an exploded view of internal components in the handle.
Figure 7B:
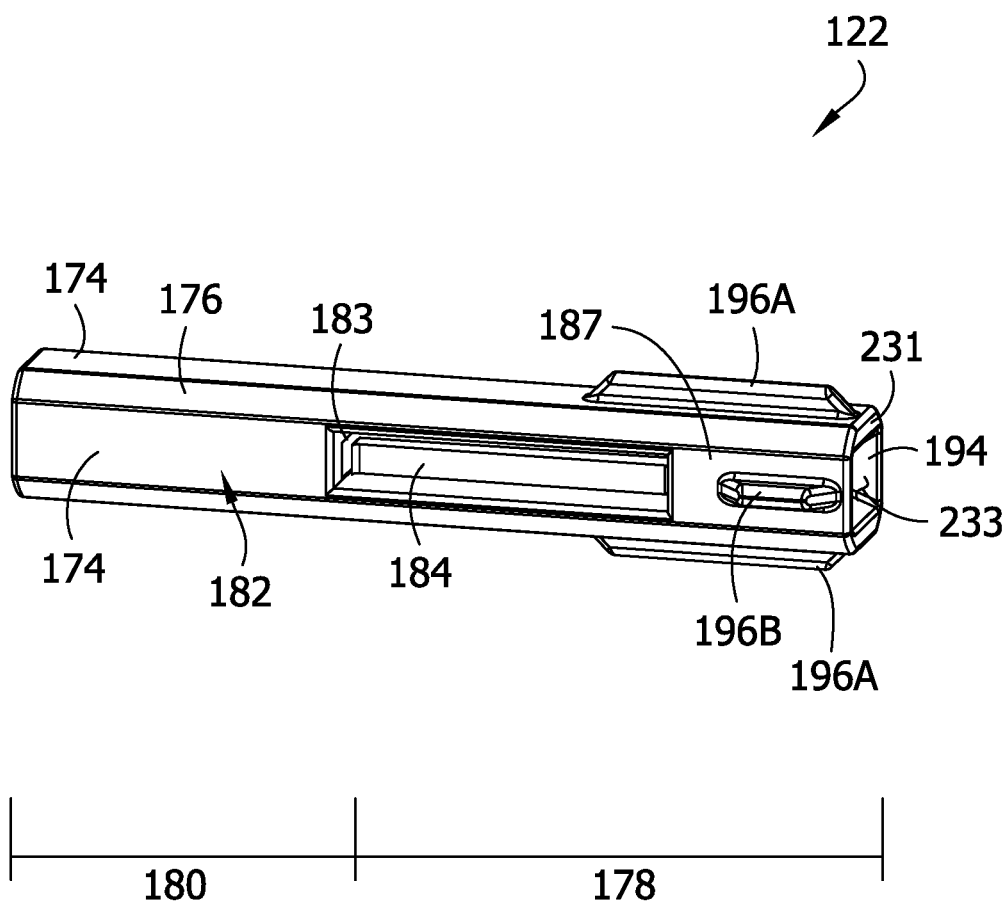
FIG. 7B is a perspective of a coupling sleeve in the handle.
Figure 8:
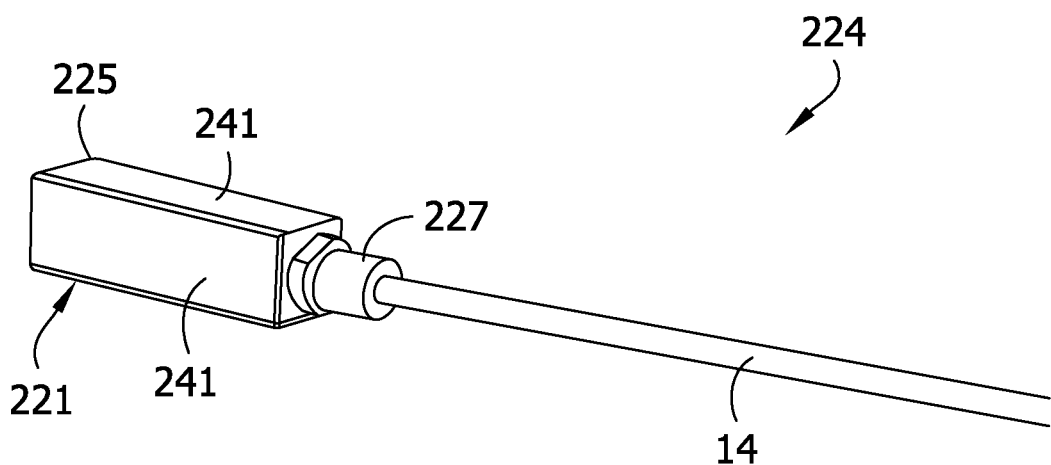
FIG. 8 is a fragmentary perspective of a liner assembly of the catheter.
Figure 9:
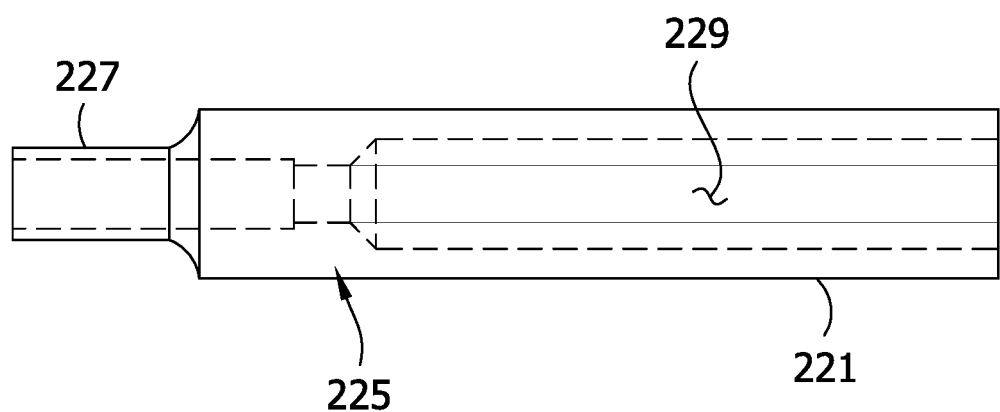
FIG. 9 is a cross section of a liner key of the liner assembly.

Referring to FIG. 7A, a guidewire port 47 is mounted on a proximal end of the buckle tube 71. In one embodiment, the guidewire port 47 is overmolded onto the buckle tube 71. Alternatively, the guidewire port 47 may be press fit onto the buckle tube 71. The guidewire port 47 provides structure in the handle 40 to support the guidewire at the proximal end of the handle. The guidewire port 47 defines an axial passage 152 through which the guidewire 26 extends. Additionally, a guidewire lock may be provided in the guidewire port 47 to lock the guidewire 26 in place relative to the handle. The guidewire port 47 may also facilitate flushing of the inner liner 14 by passing a cannula through the guidewire port and into the liner key to allow for flushing.

The guide tube 223 extends from the gearbox housing 55 at a distal end of the guide tube to a coupling sleeve 122 at a proximal end of the guide tube. The guide tube 223 is fixedly attached to the gear box housing 55, and the coupling sleeve 122 is fixedly attached to the guide tube 223. In one embodiment, the coupling sleeve 122 is press fit onto an outer surface of the proximal end of the guide tube 223. However, the coupling sleeve 122 can be attached to the guide tube 223 by any suitable means. The coupling sleeve 122 is movably received in the buckle tube 71. The engagement between the coupling sleeve 122 and the buckle tube 71 permits the coupling sleeve and guide tube 223 to translate relative to the buckle tube but prevents rotation of the coupling sleeve and guide tube 223 relative to the buckle tube. In particular, an interior passage in the buckle tube 71 provides sufficient clearance to receive the coupling sleeve 122 for axial movement but does not allow rotational movement of the coupling sleeve in the buckle tube. In one embodiment, axial translation of at least about 70 mm is permitted.

Referring to FIGS. 7A-9, a liner key 221 is attached to a proximal end of the liner 14 and is received in the coupling sleeve 122 securing the liner key to the coupling sleeve. The liner key 221 may be secured to the coupling sleeve by any suitable means, including without limitation, rotational locking, snap fit, friction fit or a press/glue/thermal bond. Thus, movement of the coupling sleeve 122 in the buckle tube 71 causes a corresponding movement of the liner key 221. The liner key 221 can also facilitate flushing of the inner liner 14. The liner 14 extends distally from the liner key 221 through the guide tube 223. The liner 14 and liner key 221 may be broadly considered a liner assembly 224. In the illustrated embodiment, the liner key 221 comprises a locking member 225 and an elongate extension member 227 extending distally from a distal end of the locking member. A channel 229 extends through the liner key 221. The proximal end of the liner 14 is attached to the extension member 227 to secure the liner to the liner key 221. Thus, the liner key 221 and the liner 14 move together as a single unit. In one embodiment, the liner 14 is received in a portion of the channel 229 extending through the extension member 227. The liner 14 can be retained in the liner key 221 by any suitable means, including without limitation, glue, thermal bond, and mechanical bond. In the illustrated embodiment, the locking member 225 comprises a cuboidal structure comprising four flat surfaces 241. However, the locking member 225 may have other shapes without departing from the scope of the disclosure. In one embodiment, the locking member 225 has a non-circular or non-rounded exterior shape. It is envisioned that the liner key 221, guide tube 223, and buckle tube 71 can have other configurations for permitting relative translation and preventing relative rotation. Further, any suitable materials may be used for the liner key 221, guide tube 223, and buckle tube 71. For example, the liner key 221, can be formed from Peek, Polyoxymethylene (POM), or polycarbonate (PC).

To assembly the liner assembly 224 in the catheter 10, the liner assembly is inserted into a distal end 232 of the coupling sleeve 122 to secure the liner assembly to the coupling sleeve. In particular, the liner 14 is first inserted into a distal opening (not shown) in the coupling sleeve 122 and pulled through a proximal opening 233 of the coupling sleeve until the liner key 221 is located adjacent the proximal opening. As will be explained in greater detail below, the coupling sleeve 122 receives the liner key 221 within the coupling sleeve by snap-fit engagement to restrict movement of the liner key relative to the coupling sleeve. Further, the coupling sleeve 122 is configured to allow the liner key 221 to enter the coupling sleeve at any entry angle, and centers the guide tube 223 within the buckle tube 71 which in turn centers and aligns the liner 14 within the drive coil 12. Thus, the liner 14 is prevented from being damaged by the drive coil 12 rotating around the liner.

In the illustrated embodiment, the coupling sleeve 122 comprises an elongate member having a generally rectangular shape defining four planar side surfaces 174. The corners of the elongate member are truncated defining four angled corner surfaces 176 connecting adjacent side surfaces 174. The coupling sleeve 122 includes a proximal portion 178 and a distal portion 180 extending distally from the proximal portion. In the illustrated embodiment, a guide tube section 182 defines the distal portion 180 of the coupling sleeve 122. The guide tube section 182 defines a guide tube passage 183 extending through the guide tube section from a distal end of the guide tube section to a proximal end of the guide tube section. The guide tube passage 183 receives a proximal end of the guide tube 223 whereby the guide tube is fixedly attached to the coupling sleeve 122. In one embodiment, the guide tube 223 terminates at a dead stop (not shown) in the guide tube section 182 to limit insertion depth of the guide tube. Arms 184 include a first portion projecting axially from a proximal base section 187, and a second portion at a distal end of the first portion projecting radially inward from the first portion. The arms 184 are configured to capture the liner key 221 within the coupling sleeve 122. For instance, when the liner key 221 is inserted into the distal opening of the coupling sleeve 122, the liner key engages the arms 184, and in particular the second portion of the arms, causing the arms to deflect outwards to provide clearance for the liner key and thereby permit the key to move past the second portion of the arms. Once the liner key 221 is fully inserted into the coupling sleeve 122 such that an entirety of the locking member 225 is disposed proximally of the second portion of the arms 184, the arms move back to their natural state preventing the liner key from being pulled back out of the distal end of the sleeve. The size and configuration of the locking member 225 of the liner key 221 and the proximal base section 187 of the coupling sleeve 122 is such that the liner key is held between the arms thereby capturing the key within the sleeve 122. More particularly, a size of the proximal opening 233 in the proximal base section 187 may narrow adjacent the arms 184 such that the locking member 225 cannot pass through the proximal opening preventing the liner key 221 from being inserted out of the proximal end 231 of the coupling sleeve 122. In one embodiment, the locking member 225 of the liner key 221 is captured in the sleeve 122 with a degree of play allowing for movement of the key in the proximal and distal directions. As such, movement of the locking member 225 may be limited in the distal direction by the second portion of the arms 184, and limited in the proximal direction by the proximal base section 187 of the coupling sleeve 122. The allowance of the small amount of movement of the liner key 221 in the coupling sleeve 122 provides assembly tolerance for the catheter components.

First external ribs 196A extend longitudinally along the top and bottom of the coupling sleeve 122, and second external ribs 196B extend longitudinally along the sides of the sleeve. Each external rib 196A, 196B extends generally from the proximal end 231 of the coupling sleeve 122. In the illustrated embodiment, the external ribs 196A, 196B have a rounded outer surface. The external ribs 196A, 196B provide an effective circular profile for the coupling sleeve 122 having an effective diameter that provides a close tolerance with the inner diameter of the buckle tube 71 to center the sleeve within the buckle tube and thereby center the liner key 221 and liner 14 within the buckle tube. Thus, the liner 14 will be centered within the drive coil 12 preventing the liner from being damaged by the drive coil rotating around the liner. It will be understood that the coupling sleeve 122 could have over shapes without departing from the scope of the disclosure. For example, broadly, the coupling sleeve may have a non-circular or non-rounded exterior shape. Further, the coupling sleeve 122, guide tube 223, gearbox housing 55, and advancer frame 73 may be broadly considered a coupling assembly for coupling the liner assembly 224, including the inner liner 14, to the advancer 45.

Figure 16A:
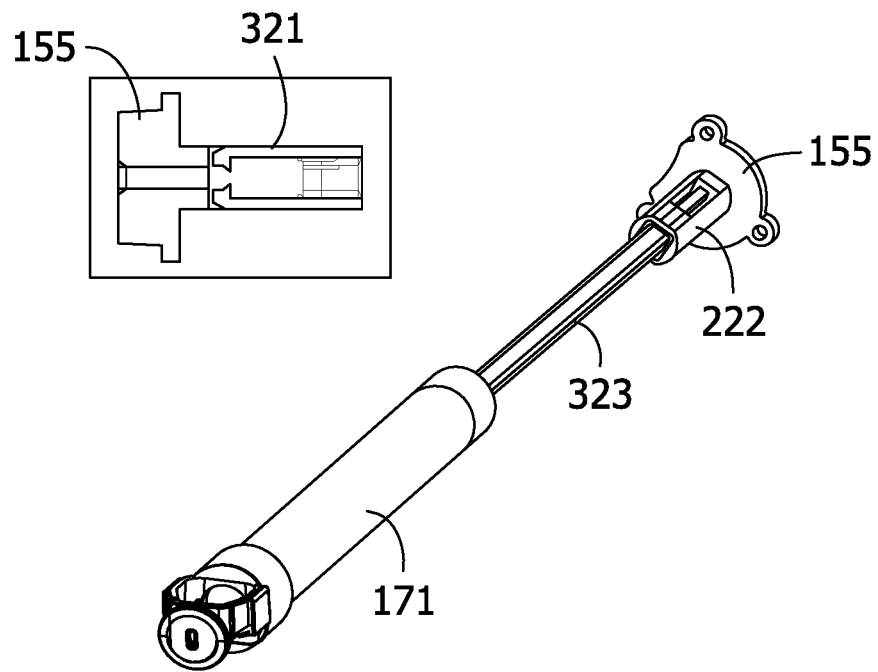
FIG. 16A is an illustration of a coupling assembly of another embodiment.
Figure 16B:
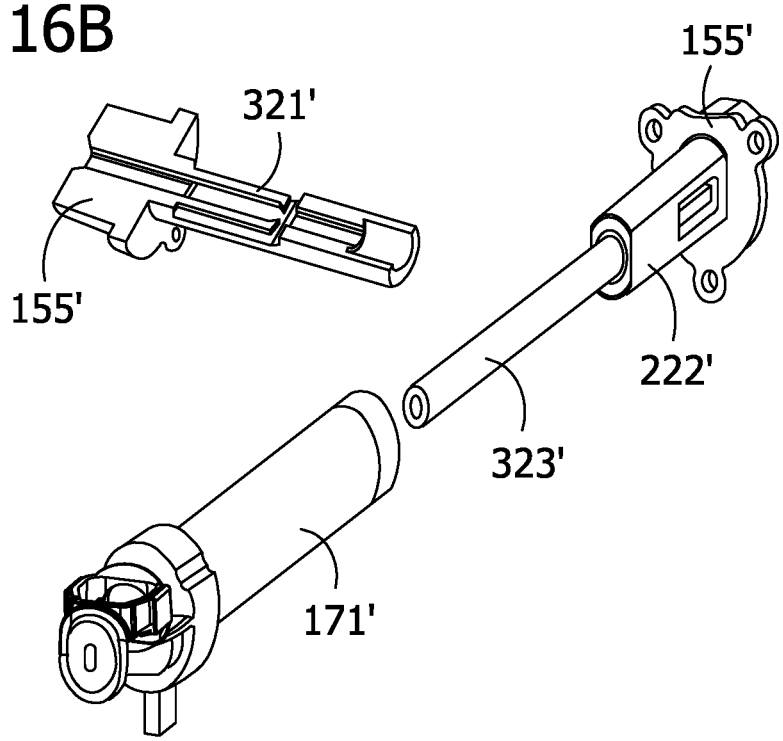
FIG. 16B is an illustration of a coupling assembly of another embodiment.

Referring to FIGS. 16A and 16B, alternative embodiments of coupling assemblies are illustrated. In this embodiment, a coupling sleeve 222, 222' is attached directly to gearbox housing 155, 155'. In the illustrated embodiments, the coupling sleeves 222, 222' are formed integrally with the gearbox housing 155, 155'. However, the coupling sleeve 222, 222' could be formed separately from the gearbox housing 155, 155' and suitably attached thereto. For example, the coupling sleeves 222, 222' may include an adaptor portion for attaching the coupling sleeve to the gearbox housing 155, 155'. Thus, the coupling sleeves 222, 222' extend directly from the gearbox housing 155, 155', and a guide tube 323, 323' extends proximally from the coupling sleeve. The coupling sleeves 222, 222' are also free of external ribs. Rather, an outer dimension of the coupling sleeves 222, 222' is sized for close tolerance inside buckle tube 171, 171'. Additionally, the sleeves 222, 222' may define both proximal and distal stop surfaces to prevent axial movement of a liner key received in the sleeve. The coupling assemblies otherwise function substantially the same as the coupling assembly of the previous embodiment.

Figure 17:
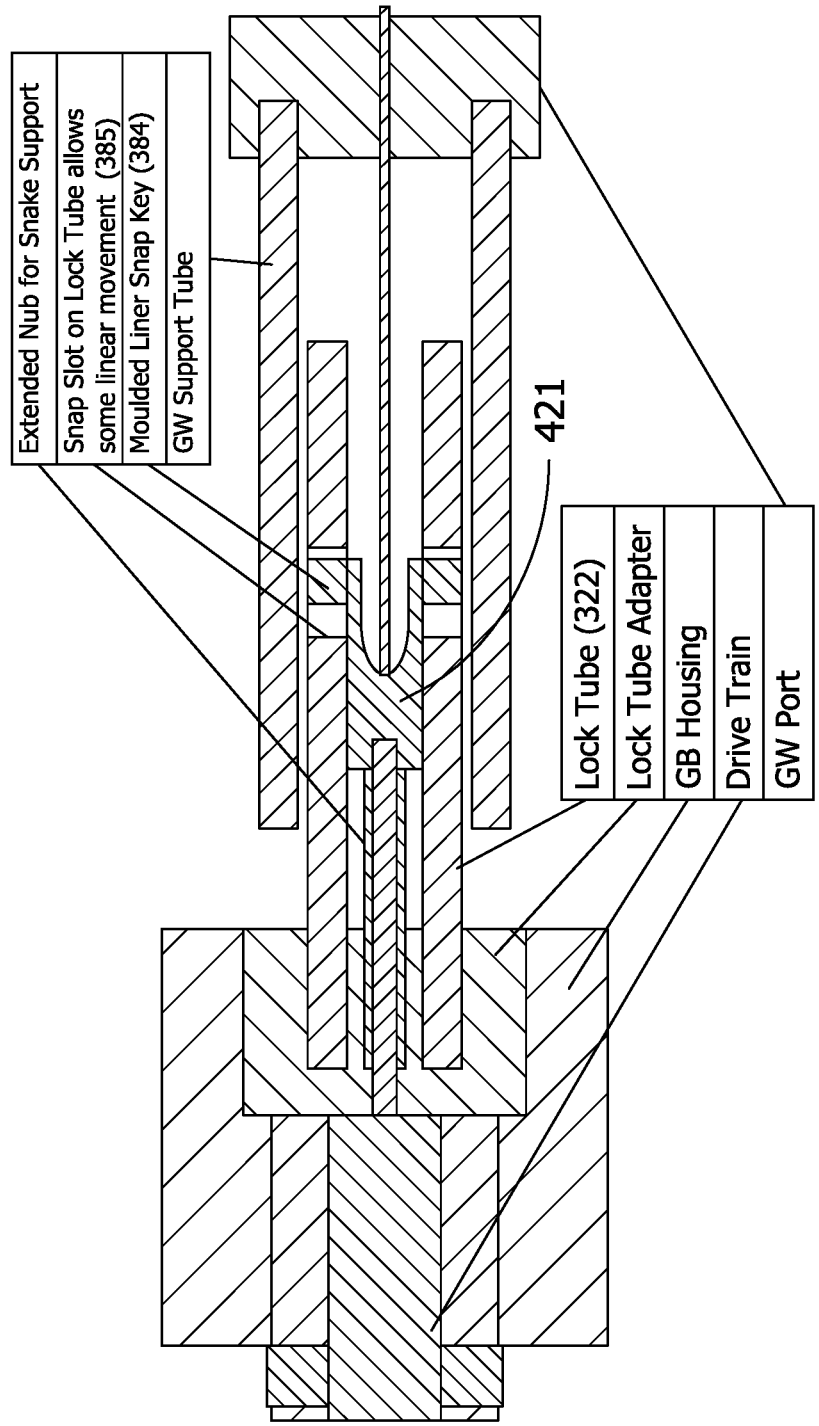
FIG. 17 is a schematic illustration of a coupling assembly of another embodiment.

Referring to FIG. 17, another alternative embodiment of a coupling assembly is illustrated. In this embodiment, liner key 421 includes arms 384 extending laterally on the key and configured for snap fit engagement with coupling sleeve 322. Thus, when the liner key 421 is inserted into the coupling sleeve 322, the arms 384 flex inward to allow for clearance to insert the key. Once the arms are placed in registration with a side opening 385 in the coupling sleeve 322, the arms 384 flex back to their natural state and become retained in the side opening thereby limiting movement of the key 421 relative to the coupling sleeve. The coupling assembly otherwise functions substantially the same as the coupling assemblies of the previous embodiments.

In the illustrated embodiment, there is a clearance between the arms 384 and the proximal and distal edges of the side opening 385. For example, there may be a 4 mm clearance (e.g., 2 mm distal and 2 mm proximal) between the arms 384 and the edges of the side opening 385. In one embodiment, there may be up to a 14 mm clearance between the arms 384 and the edges of the side opening 385. This clearance allows the liner key 421 to float relative to coupling sleeve 322 once the arms 384 are received in the side opening 385. Configuring the coupling assembly in this manner may allow for the drive coil 12 to compress prior to the inner liner 14 to relieve the axial load on the liner. This will help to alleviate an instance where compression of the inner liner 14 causes the liner to bow outward and come into contact with the other components of the catheter 10 causing wear on the inner liner. Thus, by reducing the compression of the inner liner 14 wear of the inner liner can be reduced.

Figure 18:
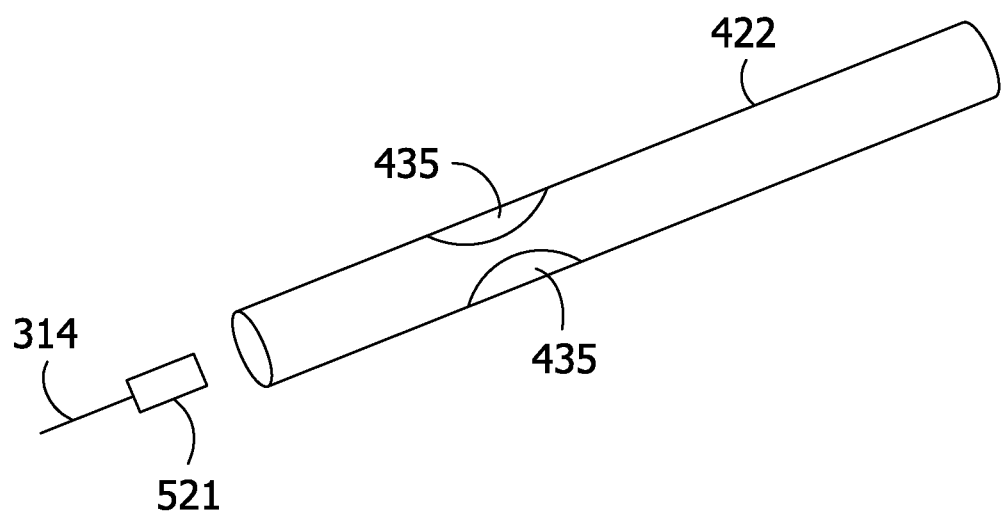
FIG. 18 is an illustration of a coupling assembly of another embodiment.

Referring to FIG. 18, another alternative embodiment of a coupling assembly is illustrated. In this embodiment, one or more magnets 435 are mounted on a coupling sleeve 422 and configured to attach to liner key 521 for securing the liner key and liner 314 to the coupling sleeve 422. In one embodiment, the liner key 521 is formed from a metallic structure so that the liner key is attracted to the magnets 435 on the coupling sleeve 422. The coupling assembly otherwise functions substantially the same as the coupling assemblies of the previous embodiments.

Figure 19A:
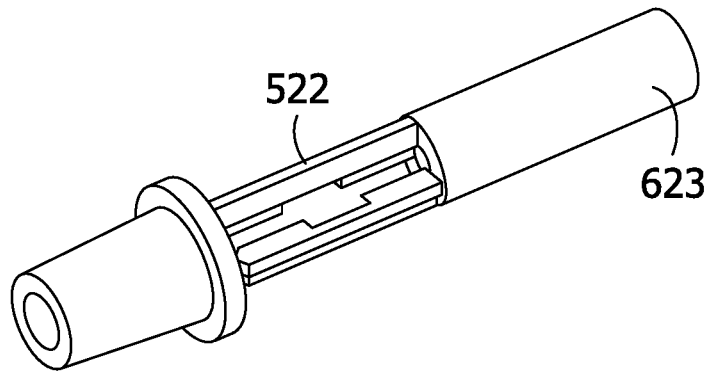
FIGS. 19A-C are illustrations of a coupling assembly of another embodiment.
Figure 19B:
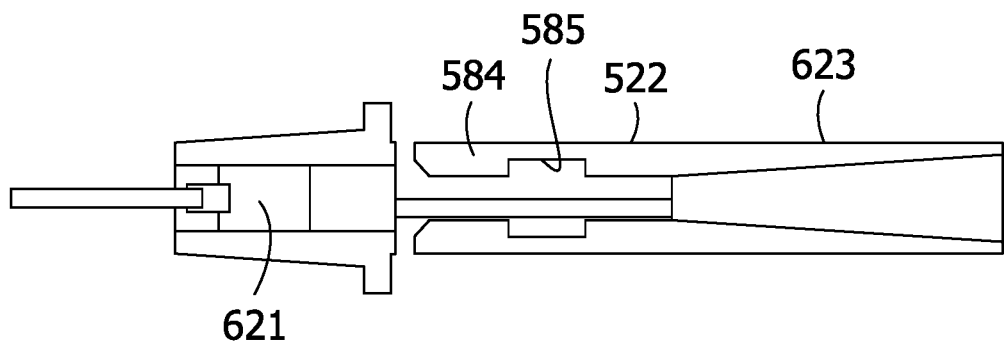
Figure 19C:
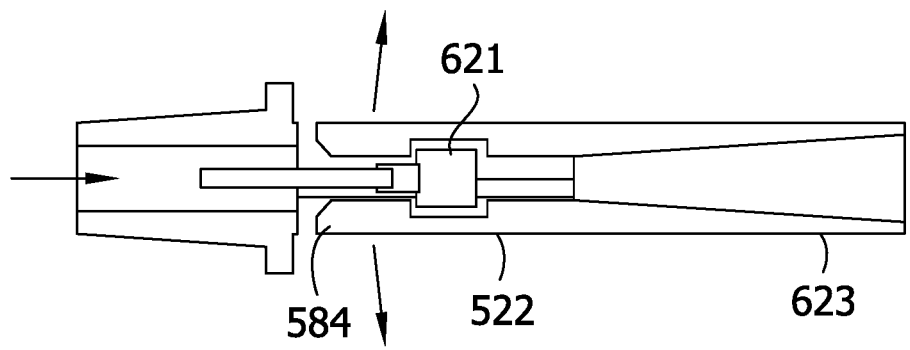

Referring to FIGS. 19A-C, another alternative embodiment of a coupling assembly is illustrated. In this embodiment, coupling sleeve 522 is formed integrally with guide tube 623. In one embodiment, the coupling sleeve 522 and guide tube 623 are injection molded together as one unitary structure. However, the components could be formed by other means without departing from the scope of the disclosure. Additionally, coupling sleeve 522 includes arms 584 configured for snap fit engagement with liner key 621. Thus, when the liner key 621 is inserted into the coupling sleeve 522, the arms 584 flex outward to allow for clearance to insert the key. Once the arms 584 are placed in registration with a recess 585 in the coupling sleeve 522, the arms 584 flex back to their natural state and become retained in the recess thereby limiting movement of the key 621 relative to the coupling sleeve. The coupling assembly otherwise functions substantially the same as the coupling assemblies of the previous embodiments.

Additionally or alternatively, arms of the coupling sleeve could engage the liner key by friction fit. Still other configurations for locking the liner ley to the coupling sleeve/guide tube are envisioned without departing from the scope of the disclosure.

Referring to FIGS. 1, and 3, the isolation sheath 22 comprises a tubular sleeve configured to isolate and protect a subject's arterial tissue within a body lumen from the rotating drive coil 12. The isolation sheath 22 is fixed to the handle 40 at a proximal end of the sheath and does not rotate. The isolation sheath 22 provides a partial enclosure for the drive coil 12 and inner liner 14 to move within the sheath. The inner diameter of the isolation sheath 22 is sized to provide clearance for the drive coil 12. The space between the isolation sheath 22 and the drive coil 12 allows for the drive coil to rotate within the sheath and provides an area for saline perfusion between the sheath and drive coil. The outer diameter of the isolation sheath 22 is sized to provide clearance with an inner diameter of a guide catheter (not shown) for delivering the catheter 10 to the desired location in the body lumen. In one embodiment, the isolation sheath 22 has an inner diameter of about 0.050 inches (1.27 mm), an outer diameter of about 0.055 inches (1.4 mm), and a length of about 1500 mm (59 inches). The isolation sheath 22 can have other dimensions without departing from the scope of the disclosure. In one embodiment, the isolation sheath 22 is made from Polytetrafluorethylene (PTFE). Alternatively, the isolation sheath 22 may comprise a multilayer construction. For example, the isolation sheath 22 may comprise an inner layer of perfluoroalkox (PFA), a middle braided wire layer, and an outer layer of Pebax.

Referring to FIGS. 1-3, the drive coil 12 may comprise a tubular stainless steel coil configured to transfer rotation and torque from the motor 43 to the tissue-removing element 20. Configuring the drive coil 12 as a coiled structure allows for the rotation and torque of the drive coil 12 to be applied to the tissue-removing element 20 when the catheter 10 is traversed across a curved path. The coil configuration of the drive coil 12 is also configured to expand its inner diameter when the coil is rotated so that the drive coil remains spaced from the inner liner 14 during operation of the catheter 10. In one embodiment, the drive coil 12 has an inner diameter of about 0.023 inches (0.6 mm) and an outer diameter of about 0.035 inches (0.9 mm). The drive coil 12 may have a single layer construction. For example, the drive coil may comprise a 7 filar (i.e., wire) coil with a lay angle of about 30 degrees. Alternatively, the drive coil 12 could be configured from multiple layers without departing from the scope of the disclosure. For example, the drive coil 12 may comprise a base coil layer and a jacket (e.g., Tecothane™) disposed over the base layer. In one embodiment, the drive coil comprises a 15 filar coil with a lay angle of about 45 degrees. The Tecothane™ jacket may be disposed over the coil. Alternatively, the drive coil 12 may comprise a dual coil layer configuration which also includes an additional jacket layer over the two coil layers. For example, the drive coil may comprise an inner coil layer comprising a 15 filar coil with a lay angle of about 45 degrees, and an outer coil layer comprising a 19 filar coil with a lay angle of about 10 degrees. Drive coils having other configurations are also envisioned.

Referring to FIGS. 1-3 and 10, the inner liner 14 comprises a multiple layer tubular body configured to isolate the guidewire 26 from the drive coil 12 and tissue-removing element 20. The inner liner 14 is extendable through the handle 40 from a position within the handle to a position distal of the handle. In one embodiment, the inner liner 14 is coupled to the components within the handle 40 but is not fixedly attached to the housing 41 to allow translation of the inner liner relative to the housing. The inner liner 14 has an inner diameter that is sized to pass the guidewire 26. The inner liner 14 protects the guidewire from being damaged by the rotation of the drive coil 12 by isolating the guidewire from the rotatable drive coil. The inner liner 14 may also extend past the tissue-removing element 20 to protect the guidewire 26 from the rotating tissue-removing element. Thus, the inner liner 14 is configured to prevent any contact between the guidewire 26 and the rotating components of the catheter 10. Therefore, any metal-to-metal engagement is eliminated by the inner liner 14. This isolation of the drive coil 12 and tissue-removing element 20 from the guidewire 26 also ensures that the rotation of the drive coil and tissue-removing element is not transferred or transmitted to the guidewire. As a result, a standard guidewire 26 can be used with the catheter 10 because the guidewire does not have to be configured to withstand the torsional effects of the rotating components. Additionally, by extending the inner liner 14 through the tissue-removing element 20 and past the distal end of the tissue-removing element, the inner liner stabilizes the tissue-removing element by providing a centering axis for rotation of the tissue-removing element about the inner liner.

Figure 10:
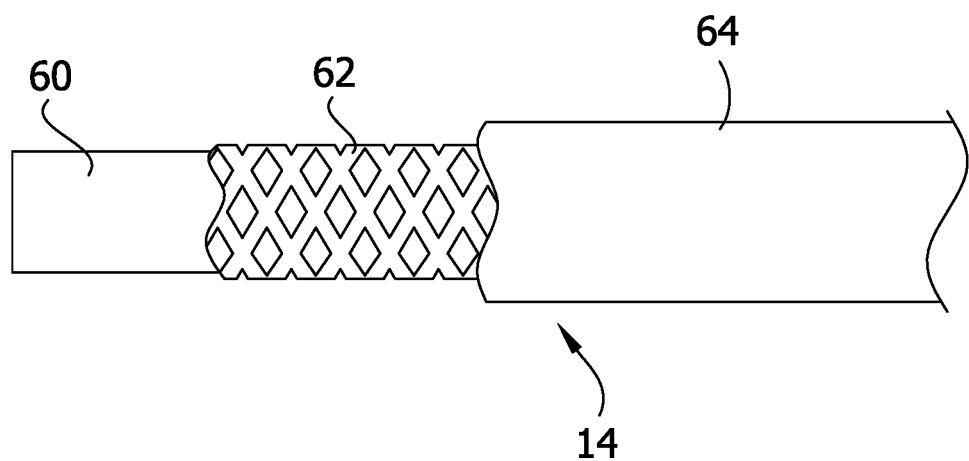
FIG. 10 is a fragmentary elevation of an isolation liner of the catheter with portions broken away to show internal details.

In the illustrated embodiment, the inner liner 14 comprises an inner PTFE layer 60 an intermediate braided layer 62 comprised of stainless steel, and an outer layer 64 of polyimide (FIG. 10). The PTFE inner layer 60 provides the inner liner 14 with a lubricous interior which aids in the passing of the guidewire 26 though the inner liner. The braided stainless steel intermediate layer 62 provides rigidity and strength to the inner liner 14 so that the liner can withstand the torsional forces exerted on the inner liner by the drive coil 12. In one embodiment, the intermediate layer 62 is formed from 304 stainless steel. The outer polyimide layer 64 provides wear resistance as well as having a lubricous quality which reduces friction between the inner liner 14 and the drive coil 12. Additionally, a lubricious film, such as silicone, can be added to the inner liner 14 to reduce friction between the inner liner and the drive coil 12. In one embodiment, the inner liner 14 has an inner diameter ID of about 0.016 inches (0.4 mm), an outer diameter OD of about 0.019 inches (0.5 mm), and a length of about 59 inches (1500 mm). The inner diameter ID of the inner liner 14 provides clearance for the standard 0.014-inch guidewire 26. The outer diameter OD of the inner liner 14 provides clearance for the drive coil 12 and tissue-removing element 20. Having a space between the inner liner 14 and the drive coil 12 reduces friction between the two components as well as allows for saline perfusion between the components.

Figure 11:
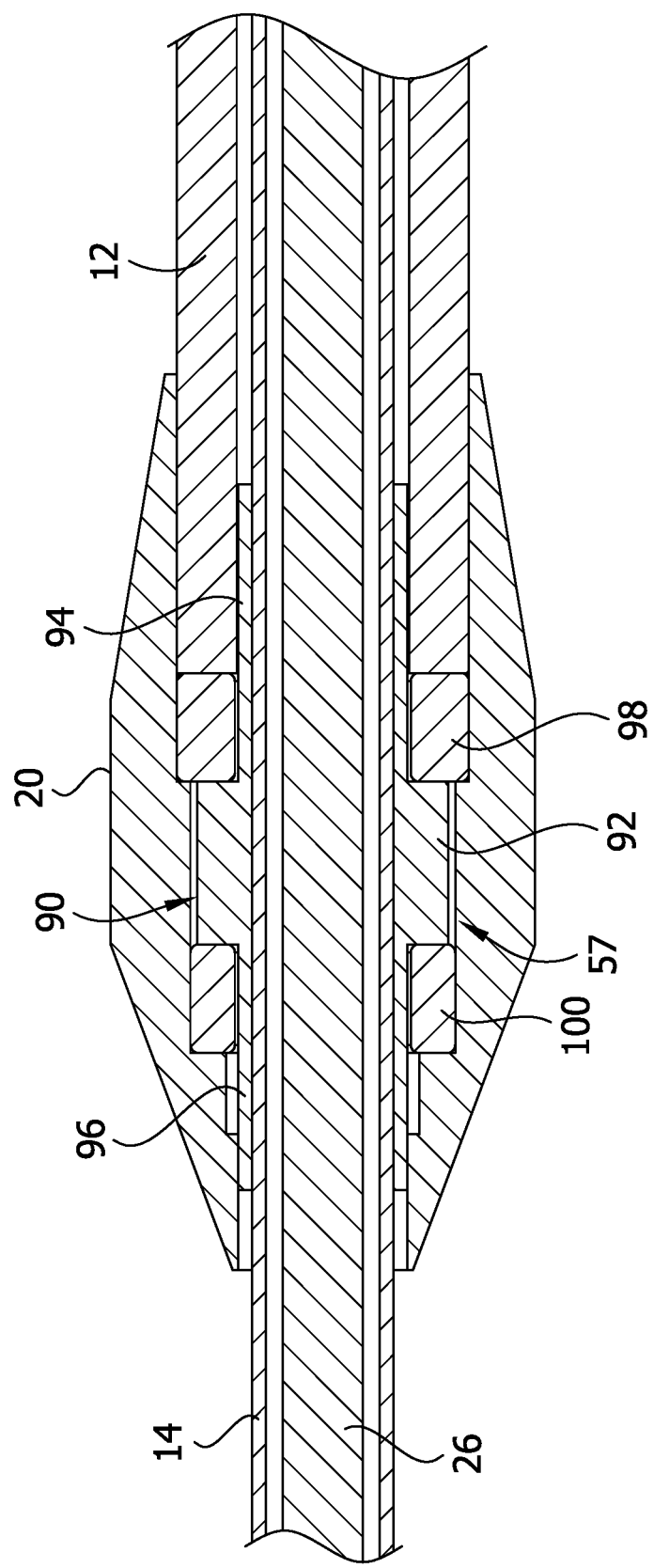
FIG. 11 is an enlarged fragmentary longitudinal cross section of the distal end portion of the catheter in FIG. 2.

Referring to FIGS. 1, 2, and 11, the tissue-removing element 20 extends along the longitudinal axis LA from a proximal end adjacent the distal end portion of the drive coil 12 to an opposite distal end. The tissue-removing element 20 is operatively connected to the motor 43 for being rotated by the motor. When the catheter 10 is inserted into the body lumen and the motor 43 is rotating the tissue-removing element 20, the tissue-removing element is configured to remove occlusive tissue in the body lumen to separate the tissue from the wall of the body lumen. Any suitable tissue-removing element for removing tissue in the body lumen as it is rotated may be used in one or more embodiments. In the illustrated embodiment, the tissue-removing element 20 comprises an abrasive burr configured to abrade tissue in the body lumen when the motor 43 rotates the abrasive burr. The abrasive burr 20 has an abrasive outer surface formed, for example, by a diamond grit coating, surface etching, or the like. In other embodiments, the tissue-removing element can comprise one or more cutting elements having smooth or serrated cutting edges, a macerator, a thrombectomy wire, etc.

Figure 12:
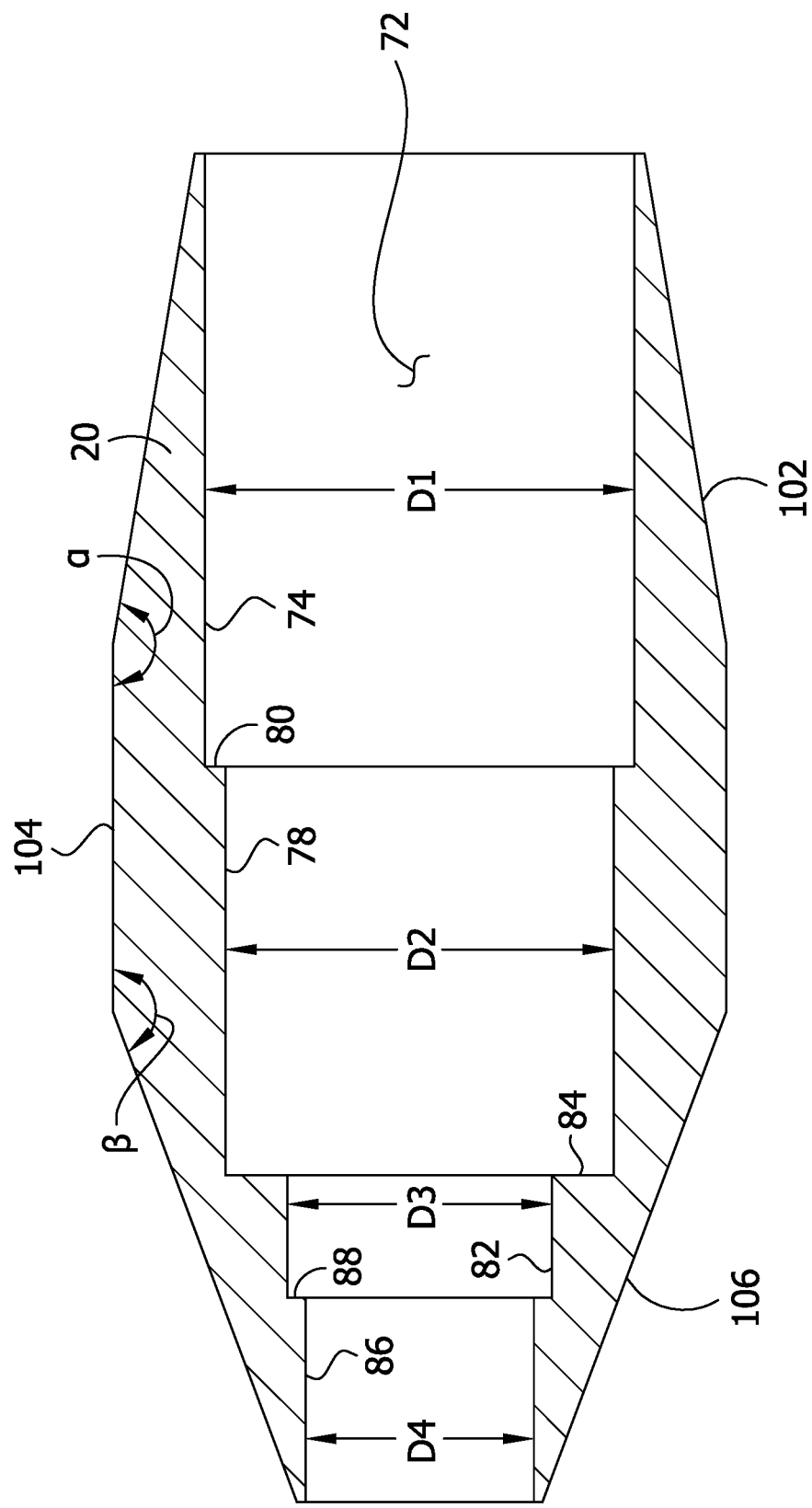
FIG. 12 is an enlarged longitudinal cross section of a tissue-removing element of the catheter.

Referring to FIG. 12, a cavity 72 extends longitudinally through the tissue-removing element 20 such that the tissue-removing element defines openings at its proximal and distal ends. The cavity 72 includes a first diameter portion 74 extending distally from the proximal end of the tissue-removing element 20 and a second diameter portion 78 extending distally from the first diameter portion forming a first shoulder 80 disposed between the first and second diameter portions. A third diameter portion 82 extends distally from the second diameter portion 78 and forms a second shoulder 84 between the second and third diameter portions. A fourth diameter portion 86 extends distally from the third diameter portion to the distal end of the tissue-removing element and forms a third shoulder 88 between the third and fourth diameter portions. The diameters of the first, second, third, and fourth diameter portions 74, 78, 82, 86 are constant along their lengths. In the illustrated embodiment, a diameter D1 of the first diameter portion 74 is larger than a diameter D2 of the second diameter portion 78, the diameter D2 is larger than a diameter D3 of the third diameter portion 82, and the diameter D3 is larger than a diameter D4 of the fourth diameter portion 86. In one embodiment, the diameter D1 of the first diameter portion 74 is about 0.037 inches (0.95 mm), the diameter D2 of the second diameter portion 78 is about 0.035 inches (0.9 mm), the diameter D3 of the third diameter portion 82 is about 0.033 inches (0.85 mm), and the diameter D4 of the fourth diameter portion 86 is about 0.031 inches (0.8 mm). Other cross-sectional dimensions are also envisioned without departing from the scope of the disclosure.

The inner liner 14 extends through the drive coil 12 and past the distal end of the tissue-removing element 20. The fourth diameter portion 86 of the cavity 72 is sized to pass the inner liner 14 with a small clearance. The inner diameter D4 provides clearance between the tissue-removing element 20 and the inner liner 14 to reduce friction between the components. Accordingly, the tissue-removing element 20 is shaped and arranged to extend around at least a portion of the drive coil 12 and inner liner 14 and thus provides a relatively compact assembly for abrading tissue at the distal end portion of the catheter 10.

Figure 13:
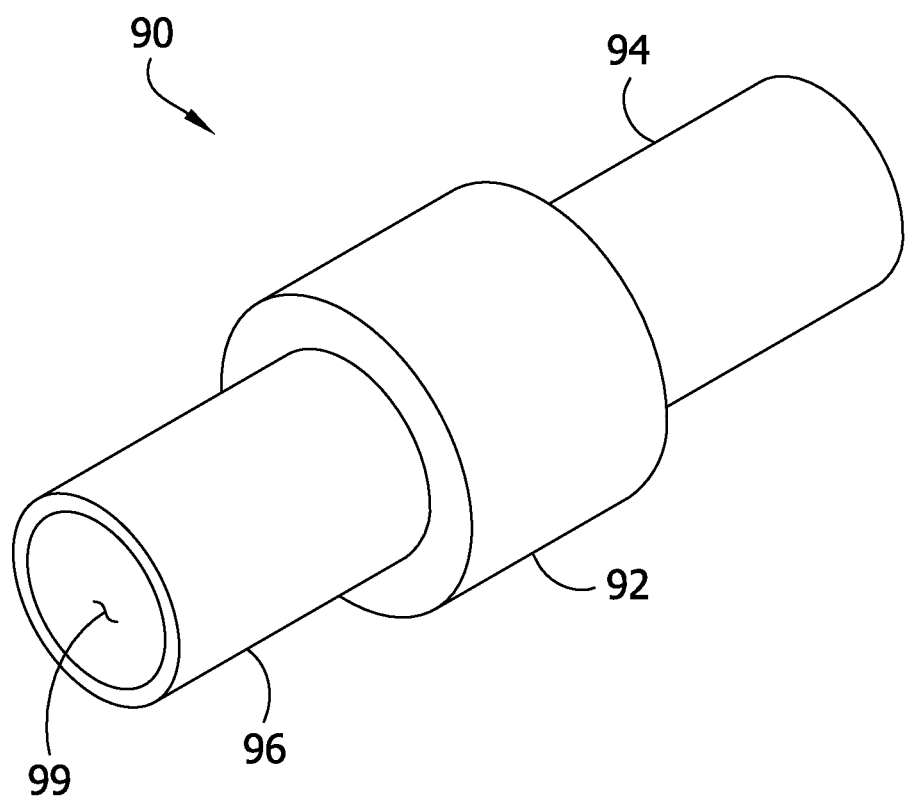
FIG. 13 is a perspective of a bushing of the catheter.

Referring to FIGS. 11-13, a bushing 90 is received in the cavity 72 of the tissue-removing element 20 and around the inner liner 14. The busing 90 comprises a center ring portion 92, a proximal ring portion 94 extending proximally from the center ring portion, and a distal ring portion 96 extending distally from the center ring portion. The ring portions of the bushing 90 define a channel 99 extending through the bushing that receives a portion of the inner liner 14. In the illustrated embodiment, the center ring portion 92 has a larger outer diameter than the proximal and distal ring portions 94, 96. The center ring portion 92 is disposed in the second diameter portion 78 of the cavity 72, the proximal ring portion 94 is disposed in the first diameter portion 74, and the distal ring portion 96 is disposed in the second and third diameter portions 78, 82. In one embodiment, the bushing 90 is made from polyetheretherketone (PEEK) and polytetrafluoroethylene (PTFE). However, the bushing 90 can be formed from other material without departing from the scope of the disclosure.

Figure 14:
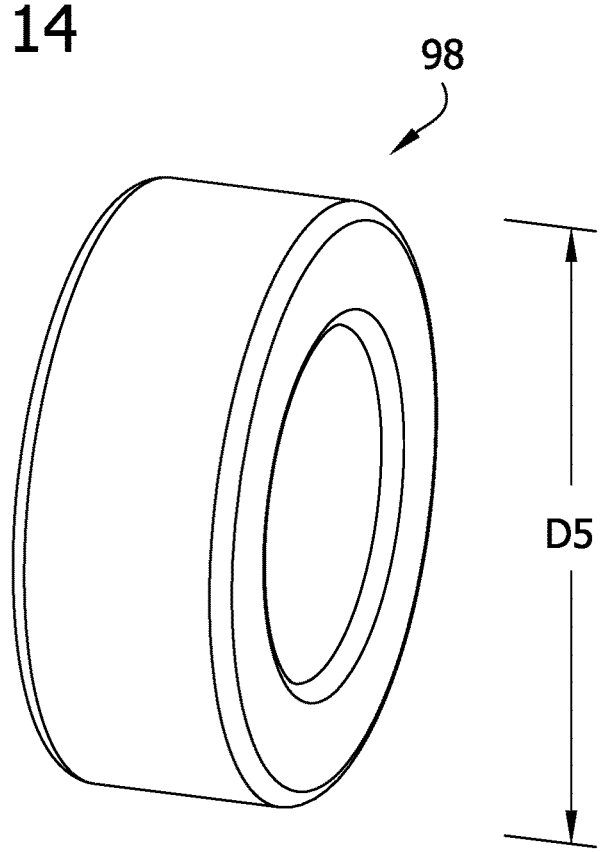
FIG. 14 is a perspective of a first bearing of the catheter.
Figure 15:
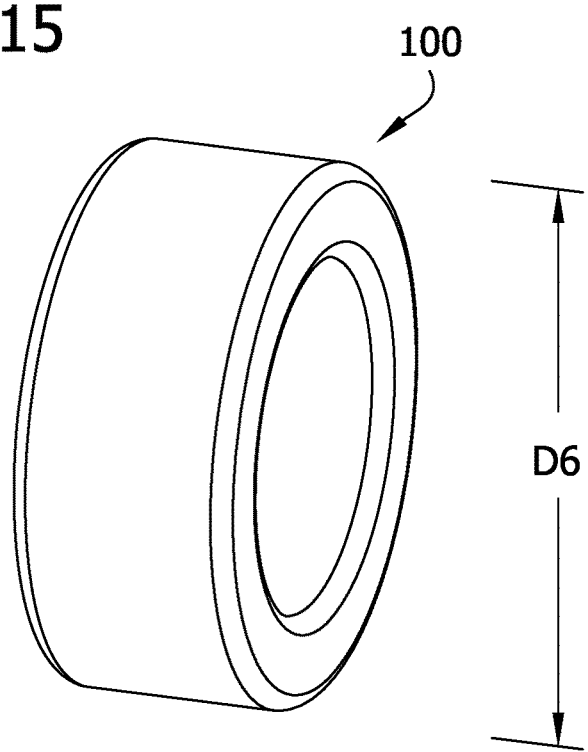
FIG. 15 is a perspective of a second bearing of the catheter.

Referring to FIGS. 11, 14, and 15, a first bearing 98 is disposed around the proximal ring portion 94 of the bearing 90, and a second bearing 100 is disposed around the distal ring portion 96 of the bearing. The first bearing 98 has an outer diameter D5 that is greater than an outer diameter D6 of the second bearing 100. In one embodiment, the bearings 98, 100 are made from Zirconia. The first bearing 98 is disposed in registration with the first diameter portion 74 of the cavity 72 in the tissue-removing element 20 and seats between a distal end of the drive coil 12 at a proximal end of the first bearing, and the center ring portion 92 of the bushing 90 and first shoulder 80 at a distal end of the first bearing. The second bearing 100 is disposed in registration with the second diameter portion 78 of the cavity 72 and is seated between the second shoulder 84 at a distal end of the second bearing, and the center ring portion 92 of the bushing 90 at a proximal end of the second bearing. As such the bushing 90 and bearings 98, 100 are held within the cavity 72 of the tissue-removing element 20. Broadly, the bushing 90 and bearings 98, 100 may be considered a coupling assembly 57 for coupling the inner liner 14 to the tissue-removing element 20.

Referring to FIG. 11, an interior surface of the bushing 90 is fixedly attached to the inner liner 14 such that the inner liner is coupled to the tissue-removing element 20 through the bushing. In one embodiment an adhesive such as an epoxy glue bonds the bushing 90 to the inner liner 14. As such, the bushing 90 does not rotate around the inner liner 14. The drive coil 12 is directly and fixedly attached to the tissue-removing element 20. The tissue-removing element 20 can be fixedly attached to the distal end of the drive coil 12 by any suitable means. In one embodiment, adhesive bonds the drive coil 12 to the tissue-removing element 20. The drive coil 12 is received in the first diameter portion 74 of the cavity 72 and a distal end of the drive coil abuts the first bearing 98. However, the inner liner 14 is not directly attached to the tissue-removing element 20, and the drive coil 12 is not directly attached to the bushing 90, bearings 98, 100, or inner liner. Thus, rotation of the drive coil 12 and tissue-removing element 20 is not transmitted to the inner liner 14 to also rotate the inner liner. Rather the tissue-removing element 20 rotates around the bushing 90 and bearings 98, 100. And because the inner liner is fixedly attached to the bushing 90, which is retained within the cavity 72 of the tissue-removing element 20 by the drive coil 12, the inner liner 14 is coupled to the drive coil and tissue-removing element through the bushing and bearing arrangement.

Further, and with reference to FIGS. 5 and 7A, fixedly attaching the guide tube 223 to the gearbox housing 55 and attaching the gearbox housing to the distal end of the advancer frame 73 couples the liner assembly 224 to the advancer frame so that the liner assembly moves along with the advancer frame. Therefore, the inner liner 14, not the drive coil 12 provides the primary push and pull force to the tissue-removing element 20 when the advancer 45 is moved relative to the handle 40. Accordingly, movement of the advancer 45 causes direct translational movement of the inner liner 14 which is then transmitted to the drive coil 12 and tissue-removing element 20. This configuration utilizes the structure of the inner liner 14 to transfer the push and pull force to the distal end of the catheter 10. The stiffness of the inner liner 14 is particular suited to efficiently transfer the pushing and pulling force to the tissue-removing element 20 without experiencing the force transfer and friction losses that can occur with using the rotating drive coil 12 to provide the push and pull force. As a result, a direct 1:1 coupling of the advancer 45 to the tissue-removing element 20 is achieved. This also allows a more flexible drive coil 12 to be used since the drive coil is not used to transfer the movement of the advancer 45 to the distal end of the catheter 10.

Referring to FIGS. 1 and 2, to remove tissue in the body lumen of a subject, a practitioner inserts the guidewire 26 into the body lumen of the subject, to a location distal of the tissue that is to be removed. Subsequently, the practitioner inserts the proximal end portion of the guidewire 26 through the guidewire lumen 24 of the inner liner 14 and through the handle 40 so that the guidewire extends through the proximal port 47 in the handle. With the catheter 10 loaded onto the guidewire 26, the practitioner advances the catheter along the guidewire until the tissue-removing element 20 is positioned proximal and adjacent the tissue. When the tissue-removing element 20 is positioned proximal and adjacent the tissue, the practitioner actuates the motor 43 using the actuator 42 to rotate the drive coil 12 and the tissue-removing element mounted on the drive coil. The tissue-removing element 20 abrades (or otherwise removes) the tissue in the body lumen as it rotates. While the tissue-removing element 20 is rotating, the practitioner may selectively move the drive coil 12 and inner liner 14 distally along the guidewire 26 to abrade the tissue and, for example, increase the size of the passage through the body lumen. The practitioner may also move the drive coil 12 and inner liner 14 proximally along the guidewire 26, and may repetitively move the components in distal and proximal directions to obtain a back-and-forth motion of the tissue-removing element 20 across the tissue by sliding the advancer 45 back and forth within the slot 186 in the handle 40. The practitioner is able to exercise a greater degree of control over the movement of the tissue-removing element 20 because the coupling between the advancer 45 and the tissue-removing element 20 to transfer the force from the advancer to the tissue-removing element is performed by the relatively stiff inner liner 14. Thus, there is no lost motion between the movement of the advancer 45 and the corresponding movement of the tissue-removing element 20. During the abrading process, the bushing 90 and bearings 98, 100 couple the inner liner 14 to the tissue-removing element 20 and allow the drive coil 12 and tissue-removing-element to rotate around the inner liner. The inner liner 14 also isolates the guidewire 26 from the rotating drive coil 12 and tissue-removing element 20 to protect the guidewire from being damaged by the rotating components. As such, the inner liner 14 is configured to withstand the torsional and frictional effects of the rotating drive coil 12 and tissue-removing element 20 without transferring those effects to the guidewire 26. Also, the coupling of the inner liner 14 and tissue removing element 20 allows for movement of the inner liner, such as translational movement within the body lumen, to be transmitted to the drive coil 12 and tissue-removing element to move the drive coil and tissue-removing element through the body lumen with the inner liner. When the practitioner is finished using the catheter 10, the catheter can be withdrawn from the body lumen and unloaded from the guidewire 26 by sliding the catheter proximally along the guidewire. The guidewire 26 used for the abrading process may remain in the body lumen for use in a subsequent procedure.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
    an elongate body having an axis, and proximal and distal end portions spaced apart from one another along the axis, wherein the elongate body is sized and shaped to be received in the body lumen;
    a handle mounted to the proximal end portion of the elongate body, the handle comprising a housing enclosing components operable to cause rotation of the elongate body;
    a tissue-removing element mounted on the distal end portion of the elongate body, the tissue-removing element being configured to remove the tissue as the tissue-removing element is rotated by the elongate body within the body lumen;
    an inner liner received within the elongate body and defining a guidewire lumen;
    an advancer mounted on the handle and movable relative to the housing;
    a guide tube within the housing of the handle and coupled to the advancer;
    a coupling sleeve within the housing of the handle and having a distal end portion coupled to a proximal end portion of the guide tube;
    a liner key received in and coupled to the coupling sleeve, wherein a proximal end portion of the inner liner is coupled to the liner key; and
    a buckle tube fixed within the housing of the handle, wherein the coupling sleeve is slidably received in the buckle tube,
    wherein movement of the advancer causes a corresponding movement of the guide tube, the coupling sleeve, the liner key, the elongate body, and the inner liner relative to the handle and the buckle tube to exert a push force on the tissue-removing element to advance the tissue-removing element and a pull force on the tissue-removing element to retract the tissue-removing element for moving the tissue-removing element relative to the handle.

2. The tissue-removing catheter as set forth in claim 1, wherein the inner liner is coupled to the tissue-removing element at a distal end portion of the inner liner.

3. The tissue-removing catheter as set forth in claim 1, wherein the coupling sleeve is fixedly attached to the liner key.

4. The tissue-removing catheter as set forth in claim 1, further comprising a motor in the handle and operatively engaging the elongate body for driving rotation of the elongate body and tissue-removing element mounted on the elongate body, wherein the advancer is operatively coupled to the motor to impart movement of the motor.

5. The tissue-removing catheter as set forth in claim 4, further comprising a gearbox housing at least partially enclosing a gear assembly operatively connected to the motor, wherein the advancer is operatively coupled to the gearbox housing to impart movement of the gearbox housing.

6. The tissue-removing catheter as set forth in claim 5, wherein a distal end of the guide tube is attached to the gearbox housing.

7. The tissue-removing catheter as set forth in claim 6, wherein the guide tube is fixedly attached to the gearbox housing.

8. The tissue-removing catheter as set forth in claim 6, further comprising a carriage mounting the motor in the handle and connecting the advancer to the gearbox housing.

9. The tissue-removing catheter as set forth in claim 1, further comprising a guidewire port mounted on a proximal end of the buckle tube.

10. The tissue-removing catheter as set forth in claim 1, wherein the coupling sleeve includes at least one magnet configured to attach to the liner key.

11. The tissue-removing catheter as set forth in claim 1, wherein the coupling sleeve attaches to the liner key by a snap-fit connection.

12. The tissue-removing catheter as set forth in claim 11, wherein one of the coupling sleeve and the liner key includes deflectable arms configured for snap-fit engagement with the other of the coupling sleeve and liner key.

13. The tissue-removing catheter as set forth in claim 1, wherein the inner liner is fixedly coupled to the elongate body at the distal end portion of the elongate body.

14. The tissue-removing catheter as set forth in claim 1, wherein the inner liner is free of direct attachment to a tissue-removing element.

* * * * *